United States Patent [19]

Cobb

[11] 4,085,130

[45] Apr. 18, 1978

[54] AMMONIALYTIC CLEAVAGE OF LACTAMS TO ω-AMINONITRILES

[75] Inventor: Raymond L. Cobb, Bartlesville, Okla.

[73] Assignee: Phillips Petroleum Company, Bartlesville, Okla.

[21] Appl. No.: 431,857

[22] Filed: Jan. 9, 1974

Related U.S. Application Data

[63] Continuation-in-part of Ser. No. 856,807, Sep. 10, 1969, abandoned.

[51] Int. Cl.² .......................................... C07C 120/08
[52] U.S. Cl. ................................ 260/465.2; 260/464; 260/465 B
[58] Field of Search .................. 260/465.2, 465 B, 464

[56] References Cited

U.S. PATENT DOCUMENTS

| | | | |
|---|---|---|---|
| 2,830,072 | 4/1958 | Garritsen et al. | 260/465.2 X |
| 3,567,757 | 3/1971 | Ida et al. | 260/465.2 |
| 3,579,558 | 5/1971 | Immel et al. | 260/465.2 |

Primary Examiner—Joseph Paul Brust

[57] ABSTRACT

Ammonialytic cleavage of lactams to ω-aminonitriles is effectively promoted by the use of catalysts selected from among molecular sieves and alkaine earth silicates. Molecular sieves additionally reduce the formation of undesired polymer.

16 Claims, No Drawings

1

AMMONIALYTIC CLEAVAGE OF LACTAMS TO ω-AMINONITRILES

This application is a continuation-in-part of Ser. No. 856,807 filed Sept. 10, 1969 now abandoned.

FIELD OF THE INVENTION

This invention relates to the production of ω-aminonitriles from the corresponding lactams. In another aspect, it relates to catalysts for the ammonialytic cleavage of lactams to ω-aminonitriles.

Lactams are internal or cyclic amides. The reaction involved utilizing the catalysts according to my invention converts the lactam to an ω-aminonitrile by a cleavage reaction involving ammonia. The reaction results in the removal of the oxygen from the lactam molecule with the formation of water, the addition of another nitrogen to the molecule, thus forming a nitrile group at one end and an amino group at the other end of a chain-like molecule. There can be various substituents along the chain.

The ω-aminonitriles are valuable chemicals since they are readily convertible to diamines or to other compounds useful as polymer precursors. For example, commercially available nylons are essentially linear long chains of amide groups

groups separated by usually 4 to 11 methylene

groups. One basic method of preparation of such nylons is by condensing the diamines with dibasic acids, for example, hexamethylene diamine with adipic acid.

It is desirable to obtain maximum conversion of lactam to the corresponding ω-aminonitrile in order to have commercially feasible production.

OBJECTS OF THE INVENTION

It is an object of my invention to provide catalysts effective to improve the ammonialytic cleavage of lactams to ω-aminonitriles.

Another object is to provide for maximum effectiveness is one or more of productivity and selectivity in the conversion of lactams to ω-aminonitriles by use of proper catalysts.

A further object is to obtain ω-aminonitrile formation while at the same time providing minimum loss to formation of undesired polymer.

Other aspects, objects, and the several advantages of my invention will be apparent to one skilled in the art from the following description and from my appended claims.

BRIEF SUMMARY OF THE INVENTION

I have discovered that the use of certain silicon-containing compounds as catalysts, more particularly the alkaline earth silicates, the Type A and Type X molecular sieves, and the mordenites, serve to enhance this ammonialytic conversion reaction.

DESCRIPTION OF THE INVENTION

The ammonialytic cleavage reaction to which I have referred can be illustrated by the following:

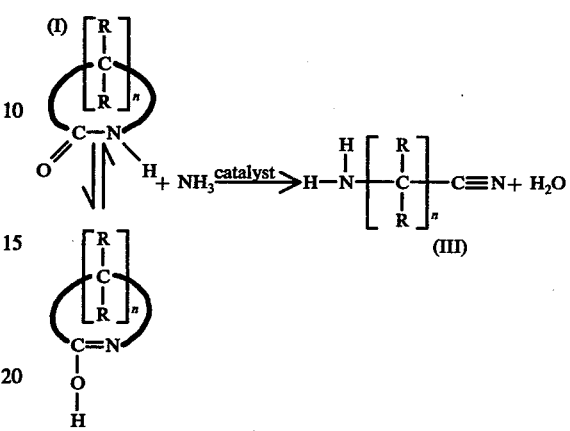

The lactam as shown by formula (I) above is called a lactim in the tautomeric or enol form as shown by formula (II) above. The reaction perhaps may be more readily visualized as being between the enol form and the ammonia. Whether the cleavage is considered as occurring on one side or the other of the nitrogen of the lactam is immaterial. The resulting noncyclic ω-aminonitrile is represented by formula (III) above.

In the lactams to which my catalysts are applicable, $n$ can be in the range of 3 to 9 inclusive in the case of application of the alkaline earth silicates and the Type X molecular sieves. The Type A molecular sieves and the mordenites are effective for a broader range of lactams wherein $n$ can be in the range of from 3 to 19 inclusive. Carbons in the chain are counted exclusive of carbons in the R groups, if any.

There can be various substituents on the carbons of the lactam ring, and consequently along the ω-aminonitrile carbon chain as shown by formula (III) above. R can be hydrogen, alkyl, cycloalkyl, aryl, or combinations thereof such as alkaryl, or aralkyl and the like, having in the range of from 1 to about 8 carbon atoms, provided that not more than 10 carbon atoms are contained in the total of R groups per lactam molecule.

EXAMPLES

The examples which follow demonstrate the operability and effectiveness of the catalysts as I apply them to the ammonialytic cleavage reaction according to the process of my invention. These examples should be considered illustrative and not limiting. The examples represent a series of runs with varying catalysts and with varying reaction temperatures. The evaluation of the results of these runs was made with the aid of analysis by gas-liquid chromatography (GLC). With this procedure, the chromatography peaks corresponding to reactants and products were identified and compared with one another on the basis of area percent, the area for each effluent constituent being defined by the base line of the chromatographic curve and the chromatographic peak for that constituent. While area percent is not necessarily identical with weight percent or mole percent, it is, nevertheless, a commonly used and reliable method for comparing the relative effects of reaction variables, such as different catalysts, within a given reaction system.

In the examples, conversion was determined by subtracting the area percent of lactam in the effluent from the catalyst-containing reactor, based on the total area of the effluent excluding ammonia, from 100. Stream selectivity was determined by calculating the area percent of the effluent from the reactor, excluding ammonia and lactam, which was the desired ω-aminonitrile.

The stream from the catalyst-containing reactor was periodically subjected to gas liquid chromatography. A lack of a peak for the original lactam showed complete conversion. The formation of polymer was measured by physically distilling representative samples to determine volatiles and nonvolatiles and the weight percent of lactam converted to polymer was thus determined. The gas liquid chromatography peak for ω-aminonitrile determines the area percent of ω-aminonitrile in the stream portion made up of the ω-aminonitrile plus unsaturated nitrile. Thus the percent of polymer subtracted from 100 times the stream selectivity is equal to selectivity percent, or of the percent of lactam converted which is converted to aminonitrile.

A series of products formed in the ammonialytic cleavage of a lactam, including the desired ω-aminonitrile, a series of minor amounts of intermediates of an unsaturated type which can be represented by

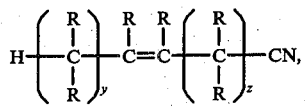

wherein $y$ and $z$ are integers such that $y + z + 2 = n$, as well as polymer, unconverted lactam, ammonia, and diluent if any. Where a diluent is used, the diluent was excluded in calculating conversion and the selectivities.

EXAMPLE I

A solution was prepared composed of 40 weight percent of the caprolactam and 60 weight percent of benzene as diluent. This solution was then admixed with ammonia by conducting the solution through a conduit equipped with a T connection to permit admixture of the ammonia and to permit closer monitoring of flow rates of the solution, the ammonia, and the admixture. The admixture was charged to a reactor at the rate of 0.5 ml per minute for the solution and at the rate of 1.9 grams per minute for the ammonia. The ammonia being admixed was at atmospheric pressure and at room temperature.

The reactor was a stainless steel reactor 1-inch in diameter containing 100 cc of magnesium silicate as the catalyst. The catalyst charged in the vertical tube reactor was retained by a plug of glass wool and some alpha-alumina at the bottom of the reactor. This run was designated Run 1.

The temperature of the reactor was controlled and varied by an electric furnace in which the reactor was contained. Thus, the stream of ammonia and lactam vapor mixture was passed through the catalytic reactor for about 20–30 minutes, the reaction temperature was noted, and the reactor effluent was sampled for analysis by gas-liquid chromatography. This process was repeated for several reaction temperatures, samples being taken at about 275°, 300°, 330°, 360°, 400°, and 425° C. The conversion and selectivity results obtained at each temperature in this series was plotted on a graph as a function of reaction temperature. At a point corresponding to 375° C reaction temperature, the curve indicated a 95 percent conversion and a selectivity of about 100 percent of lactam converted to omega aminonitrile. No polymer was formed.

The magnesium silicate used in Run 1 as an example of the alkaline earth silicates was a commercial magnesium silicate catalyst obtained from the Floridin Company of Dallas, Tex. This magnesium silicate has the formula $Mg_3Si_4O_{11} \cdot H_2O$, classified as a talc.

The above example, Run 1, shows that an alkaline earth silicate was highly effective in the desired aspects of conversion and in selectivity in converting a lactam to an ω-aminonitrile.

EXAMPLE II

A solution was prepared composed of 10 weight percent dodecano-lactam and 90 weight percent of toluene as diluent. This solution was preheated at 100° C. The preheated solution was then admixed with ammonia gas at about 400 psig and about 100° C. in the same manner as described in Run 1 in Example I above.

The solution was charged to a catalyst-containing reactor at the rate of 8 ml per minute. The ammonia was charged at the rate of 3 ml per minute measured on the basis of volumes of liquid anhydrous ammonia.

The reactor was a stainless steel reactor 1.25-inch in diameter containing 250 cc of catalyst for each run. The reactor was maintained at approximately 300°–380° C. based on the temperature measured in the middle of the bed. The admixture of lactam, diluent, and ammonia being fed to the hot reactor vaporized on contact therein. The effluent from the reactor was periodically analyzed by means of a gas liquid chromatograph. Results obtained for several runs under these conditions using several catalysts are shown in Table 1 following.

Table 1

| Run No. | Catalyst | Conversion % | Stream Selectivity % | Polymer % | Selectivity % |
|---|---|---|---|---|---|
| 2 | 3A Molecular Sieve (a) | 100 | 99 | 12 | 87 |
| 3 | 4A Molecular Sieve (a) | 100 | 99 | 17 | 82 |
| 4 | 5A Molecular Sieve (a) | 100 | 97 | 20 | 78 |
| 5 | Mordenite (b) | 100 | 99 | 20 | 79 |
| 6 | α-Alumina (c) | 55 | 95 | 3 | 92 |

(a)3A, 4A, 5A are designations of various commercially available molecular sieves. The molecular sieves used in the runs were obtained from the Linde Division, Union Carbide Corporation. The A series is a specific group of molecular sieves described hereinafter.
(b)A synthetic molecular sieve Zeolon-H (trademark) from The Norton Company, Worcester, Massachusetts described in the Norton Product Information Bulletin of January 28, 1966, described as $M_{8/n} \cdot Al_8 \cdot Si_{40}O_{96} \cdot 24H_2O$, where M may be Sodium, hydrogen, or other exchangable cation, and n is the valence of such cation, a type of mordenite. The H designation refers to the form where M equals hydrogen. The mordenite used in this run had a pore size of about 10 A.
(c) α-Alumina, obtained from the Harshaw Chemical Company, Cleveland, Ohio, was a tableted, sintered α-alumina containing 99 percent $Al_2O_3$, remainder moisture.

The data summarized in Example II, Table 1 above demonstrates the high conversion obtained by the catalyst according to the process of my invention as opposed to the relatively low conversion using α-alumina.

EXAMPLE III

Additional runs were made using the procedure and reactants as described in Example II above, except that the lactam diluent solution was charged to the catalytic reactor at a rate of 3 ml per minute. The ammonia was charged to the reactor at a rate of 1 ml per minute, and temperatures for the runs were approximately 400°–500° C. based on the temperature measured in the middle of the bed. The results for the several runs under these conditions are shown in the following table:

Table 2

| Run No. | Catalyst | Conversion % | Stream Selectivity % | Polymer % | Selectivity % |
|---|---|---|---|---|---|
| 7 | 3A Molecular Sieve[a] | 100 | 90 | 26 | 67 |
| 8 | 4A Molecular Sieve[a] | 100 | 95 | 33 | 64 |
| 9 | α-Alumina[b] | 60 | 80 | 11 | 71 |
| 10 | Glass Beads[c] | 1 | Nil | 1 | Nil |

[a] Refer note (a) in Table 1.
[b] Refer note (c) in Table 1.
[c] Laboratory type soft silica glass boiling beads.

The runs shown in Table 2 of Example III demonstrate the high conversion of lactam to ω-aminonitrile in the presence of the catalysts according to the process of my invention, as opposed to the low conversion, lower stream selectivity, in a control run with α-alumina, and particularly as compared to a control run with another silicon-containing material, i.e., glass beads, which is shown to be completely ineffective.

The runs of Example II, Table 1, and Example III, Table 2, further demonstrate that these molecular sieves are effective to show high conversion with minimal formation of polymer.

EXAMPLE IV

In the runs summarized in Table 3 below, the procedure followed was to heat caprolactam to a molten state at a temperature of 130° C. and to hold it at this temperature while 1.9 grams of ammonia gas per minute were passed through the molten lactam, with the ammonia gas at atmospheric pressure and at room temperature. This produced a vaporous mixture of lactam and ammonia containing in the range of between 75 and 100 moles of ammonia per mole of lactam. The vaporous mixture was passed through a stainless steel catalyst-containing reactor. The reactor was 1-inch in diameter and contained 100 cc of catalyst for each run.

In a manner similar to that of Example I, about 5–6 runs were carried out at different temperatures for each catalyst tested, and a performance profile was plotted on a graph with conversion and selectivity plotted as functions of reactor middle temperature. To compare the effectiveness of the catalyst, the conversion and selectivity were read from each curve at a point corresponding to 375° C reaction temperature. These standardized and directly comparable data so obtained by these series of reactions are shown in Table 3 below.

Table 3

| Run No. | Catalyst | Conversion % | Stream Selectivity % |
|---|---|---|---|
| 11 | 4A Molecular Sieve[a] | 53 | 100 |
| 12 | 13X Molecular Sieve[a] | 57 | 82 |
| 13 | γ-Alumina[b] | 90 | 25 |
| 14 | Magnesium phosphate[c] | 47 | 98 |

[a] Refer note (a) in Table 1.
[b] γ-Alumina, obtained from the Harshaw Chemical Company, Cleveland, Ohio, was in the form of ⅛-inch tablets.
[c] Magnesium phosphate pelleted, laboratory grade $Mg_3(PO_4)_2 \cdot 5H_2O$.

The above runs demonstrate that molecular sieves, both Type A and Type X, are effective catalyst for caprolactam which is a lactam with a total of 6 carbon atoms, wherein n equals 5 according to formula (I) given hereinbefore. The further run in this example shows the relatively poor stream selectivity of γ-alumina catalyst, and relatively poor conversion resulting from use of magnesium phosphate as catalyst. Only the molecular sieves in these comparative runs demonstrated effectively improved conversion plus improved stream selectivity.

Lactams

The group of lactams wherein n is in the range of about 3 to 9 include the following as illustrative examples:

6-aminohexanoic acid lactam
4-aminobutyric acid lactam
10-aminodecanoic acid lactam
10-amino-3-ethyl-5-octyldecanoic acid lactam
4-amino-2-methylbutyric acid lactam
10-amino-3-cyclohexyldecanoic acid lactam
8-amino-4,4-dicyclopentyloctanoic acid lactam
10-amino-6-phenyldecanoic acid lactam
10-amino-4-butyl-6-phenyldecanoic acid lactam
6-amino-3-benzylhexanoic acid lactam
5-amino-4-(3-ethylcyclohexyl)pentanoic acid lactam
7-amino-5-(3,5-dimethylphenyl)heptanoic acid lactam
8-amino-3-(4-ethylcyclohexyl)octanoic acid lactam
8-amino-2,2,4,4,6,6,-hexamethyloctanoic acid lactam
9-amino-2-ethyl-3-methyl-6-phenylnonanoic acid lactam
5-aminopentanoic acid lactam and the like.

Illustrative examples of lactams which can be subjected to ammonialytic cleavage with catalysts of the Type A molecular seives and mordenite molecular sieves include all of the above as illustrative examples, plus the following to further illustrate the range of n from 3 to 19:

20-aminoeicosanoic acid lactam
20-amino-2,14,15,18-tetramethyl-3,5,15-triethyleicosanoic acid lactam
20-amino-4-benzyleicosanoic acid lactam
12-aminododecanoic acid lactam
11-aminoundecanoic acid lactam and the like.

Catalysts

To exemplify the alkaline earth silicates, magnesium silicate was used in Run 1, Example I. The alkaline earth silicates as a group are effective. These alkaline earth silicates are compounds of metals of Group II-A of the Periodic Table of the Elements as it is shown on page B-3 of the Handbook of Chemistry and Physics, 49th Edition (1968), The Chemical Rubber Company, Cleveland, Ohio. Specifically, I refer to silicates of beryllium, magnesium, calcium, strontium, and barium.

By the term "silicate," I refer to the orthosilicates, the metasilicates, and the trisilicates, and include the hydrated, partly hydrated, and anhydrous forms of any of these silicates.

Nonlimiting examples of the alkaline earth silicates to which I refer are beryllium disilicate $Be_4Si_2O_7(OH)_2$, beryllium orthosilicate $Be_2SiO_4$; magnesium metasilicate $MgSiO_3$, magnesium orthosilicate $Mg_2SiO_4$; calcium α-metasilicate and calcium β-metasilicate $CaSiO_3$, calcium diorthosilicate $Ca_2SiO_4$, calcium trisilicate $Ca_{3}SiO_5$ which is sometimes written $3CaO.SiO_2$; strontium metasilicate $SrSiO_3$; strontium orthosilicate $SrSiO_4$;

barium metasilicate $BaSiO_3$; as well as the hydrates such as $BaSiO_3.6H_2O$, and the like.

While I prefer to use the synthetically produced alkaline earth silicates, the equivalent naturally-occurring minerals also are effective. Examples of the latter include enstatite $MgSiO_3$, serpentine $Mg_3Si_2O_5(OH)_4$, clinoenstatite $MgSiO_3$, forsterite $Mg_2SiO_4$, talc $Mg_3Si_4O_{10}(OH)_2$; phenakite $Be_2SiO_4$, phenazite $Be_2SiO_4$, bertrandite $Be_4Si_2O_7(OH)_2$; wollanstonite $CaSiO_3$; and the like.

Natural or synthetic mixtures or a chemically combined earth silicate such as diopside $CaMg(SiO_3)_2$ or mellilite $Ca_2MgSi_2O_7$ are effective catalysts.

The molecular sieves or zeolites to which I refer include the zeolite A or Type A, the zeolite X, or Type X, and the mordenites. Both the A and X series are synthetic products, while mordenites are produced synthetically and also found naturally occurring.

Molecular formulas for the molecular sieves or zeolites, I use the terms synonymously, have been given as follows:

Type A: $Na_{12}[(AlO_2)_{12}(SiO_2)_{12}]27H_2O$
Type X: $Na_{86}[(AlO_2)_{86}(SiO_2)_{106}].264H_2O$
Mordenite: $Na_8[(AlO_2)_8(SiO_2)_{40}].24H_2O$ Molecular sieves are particularly described in an article by D. W. Breck, 41 *Journal of Chemical Education*, page 678 and following, (December, 1964). I specifically incorporate the material of this article for detailed descriptions of the molecular sieves involved. The material following is for brief summary reference so as not to unduly lengthen this specification.

Molecular sieves have a three-dimensional interconnecting network structure of silica and alumina tetrahedra. The tetrahedra are formed by four oxygen atoms surrounding a silicon or aluminum cation. Each oxygen has two negative charges and each silicon atom has four positive charges. The trivalency of aluminum causes the alumina tetrahedron to be negatively charged which then requires an additional anion to balance the system. The final structure generally has sodium, potassium, or calcium in the network. These cations are the exchangeable ions of the zeolite structure. Quadrivalent silicon atoms can be replaced by trivalent aluminum atoms in various ratios which then alters the crystal structure.

All of the catalysts as I have described them are solid materials. The particular physical form of the catalyst is not critical, but is chosen according to suitability for a particular catalytic reactor.

Molecular sieves are commercially available in various physical forms such as granular, ⅛-inch to ¼-inch pellets, beads, and finely divided forms of up to 200 mesh.

The alkaline earth silicates, either synthetically produced or naturally occurring, preferably are used in the form of extrudates formed into pellets or irregular lumps or granules with a particle diameter of from about 3 to 6 millimeters. The particular form of the catalyst whether in pellet or lump or granule or fine particle, as to the choice of catalyst particle size, will depend to a large extent on whether a fixed bed or fluidized bed or the like will be used in the contacting zone with the lactam vapor.

Conversion Process

The catalysts are solids. The conversion itself, the ammonialytic cleavage, usually is effected in the gaseous phase. The contacting of the gaseous phase with the solid catalyst can be any conventional means, such as by passing a gaseous stream of lactam and ammonia, optionally with a diluent, through a fixed bed catalyst, or through a fluidized bed of catalyst, or otherwise as may be convenient.

Thus, it is necessary, first, to produce a vaporous stream of the lactam. The ammonia portion of the vaporous stream can be added as the molten lactam is vaporized, or added separately after the lactam is vaporized, or added as a separate gaseous phase to a liquid lactam and diluent. For example, the lactam can be melted to form a molten or fluid state and ammonia gas passed therethrough, with the effluent vapors or gases forming a vaporous stream that is a mixture of ammonia vapor and lactam vapor. This stream is conducted to a contacting or reaction zone where the ammonialytic cleavage is promoted by the catalyst. If desired, the ammonia can be heated before passing through the molten lactam.

Alternatively, the lactam can be dissolved or dispersed in a suitable solvent, ammonia gas then passed therethrough, with the effluent gaseous stream then containing vaporized lactam, ammonia vapor, and solvent vapors. This vaporous stream is contacted with a catalyst as described hereinbefore.

A more usual procedure is to prepare the lactam-diluent solution or dispersion, admix therewith the ammonia to form a liquid-gas admixture, conduct the whole admixture to the hot contacting zone where the liquid is vaporized and ammonialytic cleavage then occurs in the vapor state.

The reaction temperatures can be in the range of about 250° to 750° C. but more preferably in the range of about 350° to 500° C. Pressures in the range of about 0.1 to as much as 1000 atmospheres can be employed in the reaction zone. More usually, the pressures are within the range of about 1 to about 100 atomspheres. Atmospheric pressure is convenient, and suitable.

The reaction can be effected in a time within a range of about 0.1 second to 10 hours, or more usually, times of between 1 and about 10 seconds are suitable to obtain desired degrees of conversion.

While a minimum reaction requirement at 1 mole of ammonia per mole of lactam is required for the ammonialytic cleavage reaction, the amount of ammonia actually employed can range from the minimum of 1 to as much as 1000 moles of ammonia per mole of lactam. Excess ammonia not consumed in the reaction can be recovered, such as by suitable condensation, and recycled for reuse. The maximum amount of ammonia employed is limited primarily by economic considerations as to quantities feasible to use and recover. More than the minimum amount of ammonia is normally employed, usually at least 10 moles per mole of lactam, since most effective cleavage is obtained thereby.

I claim:

1. A method for the production of ω-aminonitriles which comprises contacting at least one lactam with a catalyst comprising Type A molecular sieves, Type X molecular sieves, or mordenites, in the presence of at least one mole of ammonia per mole of lactam converted and under reaction conditions including temperatures and pressures sufficient to effect ammonialytic cleavage of said lactam to said ω-aminonitrile, wherein said reaction temperatures in the range of about 250° to 750° C., wherein said lactam is represented by

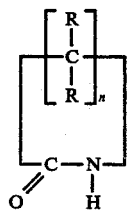

wherein R is hydrogen, alkyl, cycloalkyl, aryl, or combination thereof, having up to about 8 carbon atoms per R group and a maximum of about 10 carbon atoms in all R groups, wherein n is an integer of 3 to 19 when said catalyst comprises said Type A molecular sieve or said mordenite, and wherein n is an integer of 3 to 9 when said catalyst comprises said Type X molecular sieves.

2. A method for the production of ω-aminonitriles which comprises contacting at least one lactam with a catalyst consisting essentially of Type X molecular sieves, in the presence of at least one mole of ammonia per mole of lactam converted and under reaction conditions including temperatures and pressures sufficient to effect ammonialytic cleavage of said lactam to said ω-aminonitrile, wherein said pressure is in the range of about 0.1 to 1,000 atmospheres, said ammonia is employed in the range of about 1 to 1,000 moles per mole of said lactam, and said reaction time is in the range of about 0.1 second to 10 hours, wherein said lactam is 6-aminohexanoic acid lactam, 4-aminobutyric acid lactam, 10-aminodecanoic acid lactam, 10-amino-3-ethyl-5-octyldecanoic acid lactam, 4-amino-2-methylbutyric acid lactam, 10-amino-3-cyclohexyldecanoic acid lactam, 8-amino-4,4-dicyclopentyloctanoic acid lactam, 10-amino-6-phenyldecanoic acid lactam, 10-amino-4-butyl-6-phenyldecanoic acid lactam, 6-amino-3-benzylhexanoic acid lactam, 5-amino-4-(3-ethylcyclohexyl)pentanoic acid lactam, 7-amino-5-(3,5-dimethylphenyl)heptanoic acid lactam, 8-amino-3-(4-ethylcyclohexyl)octanoic acid lactam, 8-amino-2,2,4,4,6,6,-hexamethyloctanoic acid lactam, 9-amino-2-ethyl-3-methyl-6-phenylnonanoic acid lactam, or 5-aminopentanoic acid lactam.

3. A method for the production of ω-aminonitriles which comprises contacting at least one lactam with a catalyst consisting essentially of Type A molecular sieves or mordenites, in the presence of at least one mole of ammonia per mole of lactam converted and under reaction conditions including temperatures and pressures sufficient to effect ammonialytic cleavage of said lactam to said ω-aminonitrile, wherein said pressure is in the range of about 0.1 to 1,000 atmospheres, said ammonia is employed in the range of about 1 to 1,000 moles per mole of said lactam, and said reaction time is in the range of about 0.1 second to 10 hours, wherein said lactam is 6-aminohexanoic acid lactam, 4-aminobutyric acid lactam, 10-aminodecanoic acid lactam, 10-amino-3-ethyl-5-octyldecanoic acid lactam, 4-amino-2-methylbutyric acid lactam, 10-amino-3-cyclohexyldecanoic acid lactam, 8-amino-4,4-dicyclopentyloctanoic acid lactam, 10-amino-6-phenyl-decanoic acid lactam, 10-amino-4-butyl-6-phenyldecanoic acid lactam, 6-amino-3-benzylhexanoic acid lactam, 5-amino-4-(3-ethylcyclohexyl)-pentanoic acid lactam, 7-amino-5-(3,5-dimethylphenyl)heptanoic acid lactam, 8-amino-3-(4-ethylcyclohexyl)octanoic acid lactam, 8-amino-2,2,4,4,6,6,-hexamethyloctanoic acid lactam, 9-amino-2-ethyl-3-methyl-6-phenylnonanoic acid lactam, 5-aminopentanoic acid lactam, 20-aminoeicosanoic acid lactam, 20-amino-2,14,15,18-tetramethyl-3,5,15-triethyleicosanoic acid lactam, 20-amino-4-benzyleicosanoic acid lactam, 12-aminododecanoic acid lactam, or 11-aminoundecanoic acid lactam.

4. A method for the production of an ω-aminonitrile which comprises contacting at least one lactam with a catalyst selected from the group consisting of Type A molecular sieves, Type X molecular sieves, and mordenites, in the presence of sufficient ammonia and under reaction conditions of temperature, pressure, and time sufficient to effect ammonialytic cleavage of said lactam to said ω-aminonitrile, wherein said lactam is represented by

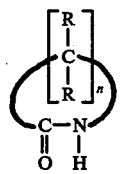

wherein R is hydrogen, alkyl, cycloalkyl, aryl, or a combination thereof, having up to 8 carbon atoms per R group, and a maximum of 10 carbon atoms in all R groups, wherein n is an integer of 3 to 19 when said catalyst is said Type A molecular sieve or said mordenite, and wherein n is an integer of 3 to 9 and when said catalyst is said Type X molecular sieve, wherein said reaction temperature is in the range of about 250° to 750° C, said pressure is in the range of about 0.01 to 1000 atmospheres, said ammonia is employed in the range of about 1 to 1000 moles of ammonia per mole of said lactam, and said contacting is conducted for a time interval of about 0.01 second to 10 hours, and wherein said ω-aminonitrile is represented by

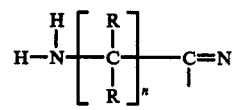

wherein R is as defined hereinabove.

5. The method according to claim 1 wherein said process comprises the steps of:
(a) converting said lactam to a liquid lactam,
(b) passing a stream of ammonia gas through said liquid lactam, thereby producing an admixture comprising said ammonia and said lactam, and
(c) contacting said admixture with said catalyst, thereby convertsaid lactam to said corresponding ω-aminonitrile.

6. The process of claim 5 wherein said step (a) is a heating step, said step (b) employs said ammonia at about 1 to about 1000 moles of said ammonia per mole of said lactam, and said contacting step (c) is conducted under a pressure of about 0.1 to about 1000 atmospheres, and during a time of about 0.1 second to 10 hours.

7. The process of claim 5 wherein said step (a) is a dissolving step employing a diluent and said lactam is substantially dispersed in said diluent such that said admixture further includes said diluent, and wherein said step (b) further employs said ammonia gas at about 1 to about 1000 moles of said ammonia per mole of said lactam; and wherein in said step (c) said contacting is at a temperature of about 250° to about 750° C.

8. The process of claim 7 wherein said admixture is vaporized prior to said contacting.

9. The process of claim 7 wherein said diluent constitutes about 1 to 90 weight percent of the total of diluent, ammonia, and lactam, and said diluent is essentially nonreactive under the said ammonialytic cleavage conditions.

10. The process of claim 9 wherein said diluent is selected from the group consisting of cyclic paraffinic hydrocarbons, aromatic hydrocarbons, cyclic ethers, mixtures thereof, and wherein said diluent contains 5 to 20 carbon atoms per molecule.

11. The process according to claim 6 wherein said lactam is caprolactam, and said catalyst is Type A or Type X molecular sieve.

12. The process of claim 7 wherein said lactam is dodecano-lactam, and said catalyst is Type A molecular sieve or mordenite.

13. The process according to claim 1 wherein said pressure is in the range of about 0.1 to 1,000 atmospheres, said ammonia is employed in a range of about 1 to 1000 moles per mole of said lactam, and wherein said reaction time is in the range of about 0.1 second to 10 hours.

14. The process according to claim 13 wherein said reaction temperature is in the range of about 350° to 500° C, and wherein said reaction pressure is substantially atmospheric pressure.

15. The process according to claim 4 wherein said lactam is caprolactam, and said catalyst is said Type A or Type X molecular sieve.

16. The process according to claim 4 wherein said lactam is dodecanolactam and said catalyst is said Type A molecular sieve or mordenite.

* * * * *

UNITED STATES PATENT AND TRADEMARK OFFICE
CERTIFICATE OF CORRECTION

PATENT NO. : 4,085,130
DATED : April 18, 1978
INVENTOR(S) : Raymond L. Cobb

It is certified that error appears in the above-identified patent and that said Letters Patent are hereby corrected as shown below:

Column 11, line 8, after "about" delete "250 to about 750°C"

and insert --- 350 to 500°C ---.

Signed and Sealed this

Twenty-second Day of May 1979

[SEAL]

Attest:

RUTH C. MASON
Attesting Officer

DONALD W. BANNER
Commissioner of Patents and Trademarks